(12) United States Patent
Andrews et al.

(10) Patent No.: US 6,350,460 B1
(45) Date of Patent: Feb. 26, 2002

(54) COSMETIC STICK COMPOSITION

(75) Inventors: Peter M. Andrews, Bangor, PA (US); Patrick Dubois, East Aurora, NY (US); Shannon Campbell, Piscataway, NJ (US)

(73) Assignee: Colgate-Palmolive Company, New York City, NY (US)

( * ) Notice: Subject to any disclaimer, the term of this patent is extended or adjusted under 35 U.S.C. 154(b) by 0 days.

(21) Appl. No.: 09/504,817

(22) Filed: Feb. 16, 2000

Related U.S. Application Data

(60) Provisional application No. 60/123,690, filed on Mar. 10, 1999.

(51) Int. Cl.$^7$ .............................. A61K 7/00; A61K 7/34; A61K 7/42; A61K 7/38; A61K 7/44
(52) U.S. Cl. .......................... 424/401; 424/66; 424/59; 424/68; 424/60
(58) Field of Search .................... 424/401, 65, 400, 424/66, 60, 70, 24, 59, 68

(56) References Cited

U.S. PATENT DOCUMENTS

| | | |
|---|---|---|
| 4,049,792 A | 9/1977 | Elsnau |
| 4,704,271 A | 11/1987 | Hourihan et al. |
| 4,822,603 A | 4/1989 | Farris et al. |
| 5,275,496 A | 1/1994 | Fattori et al. |
| 5,814,310 A | 9/1998 | Nagy et al. |
| 5,833,999 A | 11/1998 | Trinh et al. |
| 5,849,310 A | 12/1998 | Trinh et al. |
| 5,968,489 A * | 10/1999 | Swaile et al. .................. 424/65 |

FOREIGN PATENT DOCUMENTS

EP   519551 A1   12/1992

* cited by examiner

*Primary Examiner*—Thurman K. Page
*Assistant Examiner*—Blessing Fubara
(74) *Attorney, Agent, or Firm*—Rosemary M. Miano

(57) ABSTRACT

A cosmetic stick product, especially an antiperspirant and/or deodorant is disclosed which is made with a combination of dipropylene glycol, diethyl phthalate and stearyl alcohol. This stick employs the deliberate use of diethyl phthalate even in a system which is free of added fragrance to achieve improved stability and allow for the use of reduced amounts of dipropylene glycol.

16 Claims, No Drawings

COSMETIC STICK COMPOSITION

This application claims benefit of Provisional Application Ser. No. 60/123 690 filed Mar. 10, 1999.

FIELD OF THE INVENTION

This invention relates to an improved cosmetic stick made with a combination dipropylene glycol, diethyl phthalate and stearyl alcohol. This stick exhibits improved stability and allows for the use of reduced amounts of dipropylene glycol.

BACKGROUND OF THE INVENTION

Previous attempts to form stable sticks have been made using a variety of different chemistries. While ingredients such as stearyl alcohol and polyhydric alcohols such as dipropylene glycol are useful in forming cosmetic sticks such as lipsticks, sunscreens, solid perfumes, antiperspirants, deodorants, etc., there can be problems in stability which have unwanted side effects, such as high package elevating torques. This can lead to a compromise in the integrity of the product container.

Diethyl phthalate itself has previously been taught as a diluent, solubilizing agent or extender for the perfume art as in U.S. Pat. No. 5,833,999 to Trinh et al (for example, at column 4, lines 25–35) and U.S. Pat. No. 5,849,310 to Trinh et al (for example, at column 5, at 25–34).

It was noticed by us that the inclusion of fragrancing material was helpful in producing improved sticks in certain cosmetic stick products with certain chemical components. Problems sometimes arose, however, when fragrance was not included in the formulation. Since fragrance compositions sometimes contain incidental amounts of diethylphthalate ("DEP"), such as in amounts on the order of 0.02% by weight based on the total weight of the composition, it may have been this ingredient that was causing some improvement. It has now been discovered that the deliberate use of diethyl phthalate in combination with a sufficient amount of dipropylene glycol and stearyl alcohol, can be used to form satisfactory cosmetic sticks even in fragrance free products.

Thus it is an object of the present invention to create improved cosmetic sticks, especially those that are better able to be used in rigid packaging after formulation. It is a further object to form improved cosmetic sticks with reduced amounts of dipropylene glycol. These and other objects of the invention will be apparent from the following description.

SUMMARY OF THE INVENTION

The cosmetic stick compositions of the invention are made by combining:
- a) 10–24% of stearyl alcohol (particularly 18–24%);
- b) 37–55% of a volatile silicone (particularly 50–55%);
- c) 18–25% of a cosmetically active ingredient;
- d) 0.05–0.15% dipropylene glycol;
- e) 0.06–2.0% (particularly 0.10–1.0%, and more particularly 0.30–1.0%) of a co-solvent (particularly diethyl phthalate) with a solubility parameter in the range of 19–20; and
- f) 1–8% of a high melting point wax (melting point in the range of 65–102 degrees C.);

wherein the cosmetic stick has a three point flexure of at least 0.093 MPa±0.01 and an elevating torque that does not exceed 90% of the strength rating of the package in Newton-meters; and wherein all percent are weight percents based on the total weight of the composition.

DETAILED DESCRIPTION OF THE INVENTION

The importance of this invention is the creation of a more structurally desirable cosmetic stick. The use of a gellant such as stearyl alcohol in combination with a solvent such as dipropylene glycol does not always produce a product with a satisfactory shelf life as reflected in a satisfactory combination of hardness properties and elevating torque. It has been found that the use of a co-solvent such as diethyl phthalate works remarkably and surprisingly well in this system. This is in contrast to a system containing propylene glycol or tripropylene glycol which does not work satisfactorily as a substitute for dipropylene glycol in this invention. A particular embodiment of interest is a fragrance free system.

Another important aspect of this invention is that it allows for the formation of a suitable cosmetic stick with a much reduced amount of the dipropylene glycol solvent than would normally be required. For example, sticks have been made with 1/10 of the usual amount of dipropylene glycol. It has been shown that in systems that use dipropylene glycol alone as the solvent, one of two situations occur. In the first situation, if enough DPG is added to form a stick with sufficient hardness (for example, a three point flexure of at least 0.093 MPa±0.01, where when using a large sampling no more than a few percent of the data points fall below the lower limit) the elevating torque is not satisfactory (for example, it exceeds a level of 90% of the value of the strength of the package rating in N-m) resulting in a problem with the ability of the stick to be contained in the packaging. In the second situation, the amount of DPG is reduced, but the hardness of the stick is not satisfactory. This occurs even if the DPG level is reduced by only 30% of the normal amount.

Parameters for hardness and elevating torque have been described in terms of certain numerical limits (a three point flexure of at least 0.093 MPa±0.01 and an elevating torque that does not exceed 90% of the strength rating of the packaging). It should be noted, however, that the elevating torque starts out as an initial value at the time of manufacture and then increases over time depending on the amount of moisture the composition absorbs over time. The value of the elevating torque will plateau out a final value at about 6 months of age. From a statistical standpoint, the cosmetic sticks of the invention should be made so that no more that 4% of the sticks made in a given batch exhibit a three point flexure less than 0.093 MPa±0.01 and an elevating torque (after 4–6 months) that exceeds 90% of the strength rating of the package in Newton-meters.

In one particular example, a package of the type described in U.S. Pat. No. 5,275,496 (incorporated by reference in its entirety herein) can be made to withstand a force of X N-m. In that case it is preferred that the composition of the invention be made to have an initial elevating torque value (as measured within 2 weeks of manufacture) of less than X-2 N-m. For example if the packaging is rated at 4.1 N-m the initial elevating torque value should be less than 1.76 N-m. Other equivalents are possible. For example, for a package rated at being able to withstand a force of 5.1 N-m, an initial elevating torque not exceeding 2.76–2.79 may be used.

For packaging that is not completely air tight (for example, a package of the type described in U.S. Pat. No.

5,275,496), a greater increase in elevating torque can be expected over the shelf life of the product (for example, over a period of 6 months) than for more air-tight packaging. Thus, for packaging that is air-tight a higher initial elevating torque value can be tolerated, as long as the final value (for example, after a shelf life of 6 months) is less than the 90% limit described above.

With respect to the components used to make this invention, the volatile silicone may be selected from the group consisting of volatile, low, molecular weight polydimethylsiloxane materials which are either linear or cyclic, with particular example being cyclomethicone such as Dow Corning 245 Fluid, Dow Corning 345 Fluid, SF-1204 (GE Silicones) which are cyclic dimethyl polysiloxane compounds where the ring may contain from between 4–6 silicone atoms.

The cosmetically active ingredient may be selected from the group consisting of topically active compositions that act upon contact with skin or that are cosmetic enhancements in their own right such as lipsticks and eye shadow sticks. These ingredients can be added separately or added with any of the ingredients in the cosmetic stick. Examples of cosmetically active ingredients include sun screens, coloring agents, topical anesthetics, insect repellents, antimicrobial compounds, antifungal compounds, and antiperspirant actives.

Antiperspirant actives include conventional aluminum and aluminum/zirconium salts, as well as aluminum/zirconium salts complexed with a neutral amino acid such as glycine, as known in the art. See each of European Patent Application Number 512,770 A1 and PCT case WO 92/19221, the contents of each of which are incorporated herein by reference in their entirety, for disclosure of antiperspirant active materials. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, aluminum dichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as tin or titanium analogues of the aluminum salts listed above, aluminum nitratohydrate and its combination with zirconyl hydroxychlorides and nitrates, or aluminum-stannous chlorohydrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy zirconium/aluminum salt-glycine materials, having enhanced efficacy due to improved molecular distribution, known in the art and discussed, for example, in PCT No. WO92/19221, the contents of which are incorporated by reference in their entirety herein.

Antiperspirant actives can be incorporated into compositions according to the present invention in amounts in the range of 0.1–30% (on an anhydrous solids basis), preferably 5–25%, by weight, of the total weight of the composition. The amount used will depend on the formulation of the composition. For example, at amounts in the lower end of the broader range (for example, 0.1–5%), the antiperspirant active material will not substantially reduce the flow of perspiration, but will reduce malodor, for example, by acting as a deodorant material, for example, by acting as an antimicrobial or complexing with the malodorous components of human perspiration.

Deodorant active materials can include lesser amounts of antiperspirant actives, such as in the range of 0.01–10%, as well as fragrances, and effective amounts of antimicrobial agents, for example, bacteriostatic quaternary ammonium compounds (such as cetyl trimethyl-ammonium bromide, and cetyl pyridinium chloride), 2,4,4'-trichloro-2'-hydroxydiphenylether (Triclosan), N-(4-chlorophenyl)-N'-(3,4-dichlorophenyl)urea (Triclocarban), silver halides, octoxyglycerin (SENSIVA™ SC 50) and various zinc salts (for example, zinc ricinoleate) may also be included in formulations of the present invention. The bacteriostat can, illustratively, be included in the composition in an amount of 0.01–1.0% by weight, of the total weight of the composition. Triclosan or triclocarban can, illustratively, be included in an amount of from 0.05% to about 0.5% by weight, of the total weight of the composition.

Suitable co-solvents with a solubility parameter in the range of 19–20 include diethylphthalate.

Suitable high melting point waxes include hydrogenated castor oil, beeswax, spermaceti, carnauba, baysberry, candelilla, montan, ozokerite, ceresin, paraffin, synthetic waxes, microcrystalline wax, and mixtures thereof. Hydrogenated castor oil (castor wax) is the preferred high melting point wax. Such high melting point waxes that are among those useful herein are disclosed in U.S. Pat. No. 4,049,792 to Elsnan which is incorporated by reference herein in its entirety.

Optionally, one or more of the following ingredients may also be included:

1) One or more surfactants selected from the group consisting of polyoxyethylene ethers, polyoxyethylene esters, polyoxyethylene diesters, polyoxyethylene glycol ethers, polyoxyethylene glycol esters, polyoxyethylene glycol diesters, polyoxyethylene glyceryl esters, polyoxyethylene glyceryl diesters, glyceryl esters and, in particular, surfactants such as polyoxyethylene glycol esters, glyceryl esters, polyoxyethylene glycol diesters, and polyoxyethylene glycol ethers.
   (a) up to 2% PEG-100 stearate in combination with up to 2% of glyceryl monostearate; or (b) 0.5–5% PEG-8 distearate; or (c) 0.5–4% PEG-25 propylene glycol stearate.
2) Coloring agents.
3) Additional emollients which are a known class of materials in this art. According to the present invention, the emollient (for example, non-volatile emollient) incorporated in the composition both imparts desirable aesthetic properties to the stick and imparts emollient effects to the skin. Suitable non-volatile emollients include silicone and non-silicone materials. Such silicone materials include silicone compounds such as polyalkylsiloxanes, polyalkyarylsiloxanes, and polyethersiloxane copolymers. Such non-silicone materials include fatty acid, fatty alcohol esters, and water insoluble ethers and alcohols. Emollients among those useful in the art are described in *Cosmetic, Science and Technology*, Vol, 1, 27–104 (1972) edited by Balsam and Sagarin, which article is incorporated by reference herein in its entirety.

The non-volatile emollient materials (both the non-volatile silicone materials and the non-volatile emollient material that is not a silicone material) each can include a mixture.

Illustratively, the non-volatile emollient material can be incorporated in the composition in an amount of 3%–27% by weight, of the total weight of the composition. This range is not limiting of the present invention.

Particular examples of emollients include PPG-14 butyl ether in an amount of 4-15%; phenyl trimethicone in an amount of 2–10%; C12–15 alkyl benzoate such as in an amount of 4–15%; or dimethicone in an amount of 2–5%.

4) Inert particulates may also be included. These include 1–10% of inert particulates comprising materials or mixtures of materials that are essentially water insoluble and which do not decompose or react with wax, materials, silicone oils or other components of the cosmetic sticks under the conditions of preparation and of use. Among the particulates that may be incorporated in this invention include those composed of polyolefins (such as polystyrene, polyethylene, and polypropylene), nylon, Teflon®, insoluble crosslinked starches, talc, silica (including fumed and precipitated silicas), clays (including bentonites, hectorites, kaolin) talcum, etc. (see description for some of these materials in U.S. Pat. No. 4,822,603 which patent is incorporated by reference in its entirety herein). Particular examples of such materials include 2–10% talc, 1–2% polyethylene.

5) Fragrance may also be included such as encapsulated fragrance in an amount of 0.2–1.5% or conventional fragrance in an amount of 0.01–2.0%.

6) Antimicrobials may be included in both antiperspirants and deodorant compositions. One example is Triclosan as noted above, particularly in an amount of 0.093–1%.

The compositions of the invention may be made by a variety of techniques. One method is admixing the components of the formulation using sufficient temperatures to melt or dissolve the waxes in the liquid base material, pouring the composition into a stick mold (or multiple molds), and then cooling the product to form a solid stick. Typically the wax and liquid materials are mixed together at a temperature of 70–90 degrees C. and then the particulate matter is added. The batch is then cooled to 60 degrees C. and then, prior to pouring into stick molds, the composition is cooled further to just above the solidification point of the composition.

The cosmetic sticks made for this invention in general are opaque.

Particular ranges for the ratios of the DPG, DEP and stearyl alcohol to total formula weight are in the range of 0.16–0.05 DPG to 0.02–0.45 DEP where the formula weight is 1.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps. Also where a composition is described as comprising, the composition should be read as including a composition made by combining the listed ingredients even if reaction products are formed.

The following Examples are given as illustrative of the invention but other modifications may be made by those skilled in the art which are within the spirit and scope of the invention. Unless otherwise noted, all amounts in the Examples and elsewhere in the application are in weight percents. All chemical symbols and scientific abbreviations have their usual and customary meanings and all temperatures are in degrees C. Note that $MPa=1\times10^6$ Pa. The method described above was used to make the compositions with the ingredients described in the Examples unless particular modifications are described in the Examples.

EXAMPLES

Examples 1–2

Examples 1 and 2 are antiperspirant sticks made as a batch with the ingredients listed in Table I. For Examples 1 and 2 the cyclomethicone is mixed with the stearyl alcohol and the mixture is heated to about 72 degrees C. until the solution was clear. The Hydrogenated Castor Oil and Arlacel 165 is then added and mixed until dissolved. The antiperspirant active is added as dry particulate matter. The dipropylene glycol and diethyl phthalate are added and the batch is mixed. The batch is cooled with mixing to 53 degrees C., poured into stick forms, and cooled further to form a solid stick. All amounts are in weight percent based on the total weight of the composition.

TABLE I

| Ingredient | Example 1 | Example 2 |
|---|---|---|
| Cyclomethicone | 52.50 | 52.51 |
| Stearyl Alcohol | 22.00 | 22.00 |
| Hydrogenated Castor Oil | 2.00 | 2.00 |
| Aluminum Zirconium Tetrachlorohydrate Gly | 22.00 | 22.00 |
| Arlacel ® 165[a] | 1.0 | 1.0 |
| Dipropylene Glycol | 0.16 | 0.05 |
| Diethyl Phthalate | 0.34 | 0.44 |
| Total | 100.00 | 100.00 |

[a]A blend of PEG-100 stearate and glyceryl monostearate, sold by ICI Americas Inc., Wilmington, Delaware.

Examples 3–4

For purposes of comparison, the procedure of Examples 1–2 can be repeated except that the solvents or co-solvent are removed. The ingredients that can be used to make these comparable sticks are listed below in Table II.

TABLE II

| Ingredient | Example 3 | Example 4 |
|---|---|---|
| Cyclomethicone | 53.00 | 52.50 |
| Stearyl Alcohol | 22.00 | 22.00 |
| Hydrogenated Castor Oil | 2.00 | 2.00 |
| Aluminum Zirconium Tetrachlorohydrate Gly | 22.00 | 22.00 |
| Arlacel ® 165[a] | 1.0 | 1.0 |
| Dipropylene Glycol | 0.00 | 0.5 |
| Diethyl Phthalate | 0.00 | 0.00 |
| Total | 100.00 | 100.00 |

[a]A blend of PEG-100 stearate and glyceryl monostearate, sold by ICI Americas Inc., Wilmington, Delaware.

To determine the structural integrity of the sticks, the three point flexure of a cosmetic stick made according to Example 2 was compared to sticks made with the same amount of ingredients as described for Examples 3 and 4. Parameters for three point flexure as measured by the method described in ASTM C 1161-94 as well as torque to elevate the stick over time as measured by the method described in ASTM D 2063-91 were used, which published ASTM methods are incorporated by reference in their entirety herein. Measurements were taken on a number of sticks and the values reported are averages. As can be seen in Table III, dipropylene glycol results in improved stick structure, however, in the case of Example 4 this also resulted in higher elevating torques. When used at lower levels with a co-solvent, compositions can be made with good structure and low elevating torques. The package rating used for these products was 4.1N-m. Note that for Example 2, no more than 4% of the sticks failed the criteria of having (a) a three point flexure of at least 0.093 MPa±0.01 and (b) an elevating torque that is maintained at a value that does not exceed 90% of the strength rating for the package. Example 4 will not meet this test. Example 3 had a failure rate of greater than 4% for the three point flexure test even though the average value looked acceptable.

TABLE III

| Stick Sample | Three Point Flexure (average) (MPa) | Initial elevating torque (N · m) | Elevating torque after 1 month (N · m) | Elevating torque 6 months (N – m)[b] |
|---|---|---|---|---|
| Example 3 | 0.13[c] | 1.08 | 2.03 | 3.38 |
| Example 4 | 0.17 | 2.03 | 3.12 | 4.33 |
| Example 2 | 0.17 | 1.08 | 2.17 | 3.38 |

We claim:

1. A cosmetic stick composition comprising:
   a) 10–24% of stearyl alcohol;
   b) 37–55% of a volatile silicone;
   c) 18–25% of a cosmetically active ingredient;
   d) 0.05–0.15% dipropylene glycol;
   e) 0.06–2.0% of a co-solvent with a solubility parameter in the range of 19–20; and
   f) 1–8% of a high melting point wax;
   wherein the cosmetic stick has a three point flexure of at least 0.093 MPa±0.01 and an elevating torque that is maintained at a value that does not exceed 90% of the strength rating of the package in Newton-meters; and wherein all percent are weight percents based on the total weight of the composition.

2. A cosmetic stick composition according to claim 1 wherein the volatile silicone is a member of the group consisting of volatile, low, molecular weight polydimethylsiloxane materials which are either linear or cyclic.

3. A cosmetic stick composition according to claim 1 wherein the volatile silicone is cyclomethicone.

4. A cosmetic stick composition according to claim 1 wherein the cosmetically active ingredient is a member of the group consisting of sun screens, coloring agents, topical anesthetics, insect repellents, antimicrobial compounds, antifungal compounds, and antiperspirant actives.

5. A cosmetic stick composition according to claim 4 wherein the antiperspirant active is a member of the group consisting of aluminum salts, aluminum/zirconium salts, and aluminum/zirconium salts complexed with a neutral amino acid.

6. A cosmetic stick composition according to claim 5 wherein the antiperspirant active is a member of the group consisting of aluminum chlorohydrate, aluminum chloride, aluminum sesquichlorohydrate, zirconyl hydroxychloride, aluminum-zirconium glycine complex, aluminum chlorohydrex PG, aluminum chlorohydrex PEG, aluminum dichlorohydrex PG, aluminum dichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing.

7. A cosmetic stick composition according to claim 1 wherein the co-solvent is diethyl phthalate.

8. A cosmetic stick composition according to claim 5 wherein the co-solvent is diethyl phthalate.

9. A cosmetic stick composition according to claim 1 wherein the high melting point wax is hydrogenated castor oil.

10. A cosmetic stick composition according to any one of claims 1–9 which is free of added fragrance.

11. A cosmetic stick composition according to claim 1 which further comprises at least one ingredient selected from the group consisting of a surfactant, an additional emollient and an inert particulate material.

12. A cosmetic stick according to claim 1 wherein the amount of co-solvent is 0.10–1.0%.

13. A cosmetic stick according to claim 1 wherein the amount of co-solvent is 0.30–1.0%.

14. A cosmetic stick according to claim 1 wherein the amount of stearyl alcohol is 18–24%.

15. A cosmetic stick according to claim 1 wherein the amount of volatile silicone is 50–55%.

16. A cosmetic stick composition made as a batch by combining:
   a) 10–24% of stearyl alcohol;
   b) 37–55% of a volatile silicone;
   c) 18–25% of a cosmetically active ingredient;
   d) 0.05–0.15% dipropylene glycol;
   e) 0.06–2.0% of a co-solvent with a solubility parameter in the range of 19–20; and
   f) 1–8% of a high melting point wax;
   wherein at least 96% of the cosmetic sticks made in the batch have a three point flexure of at least 0.093 MPa±0.01 and an elevating torque that does not exceed 90% of the strength rating of the package in Newton-meters during the life of the product; and
   wherein all percent are weight percents based on the total weight of the composition.

* * * * *